United States Patent
Scholl et al.

[19]

[11] Patent Number: 6,042,347
[45] Date of Patent: Mar. 28, 2000

[54] PEDIA-CADIO PUMP

[76] Inventors: Frank G. Scholl, 31 Taylor Pl., Branford, Conn. 06405; Alvin A. Snaper, 2800 Cameo Cir.; Kenneth S. Scholl, 2805 Ashworth Cir., both of Las Vegas, Nev. 89107

[21] Appl. No.: 09/123,172

[22] Filed: Jul. 27, 1998

[51] Int. Cl.[7] .................................................. F04G 17/00
[52] U.S. Cl. ........................... 417/423.12; 600/16; 623/3
[58] Field of Search .............................. 417/356, 423.12; 600/16; 623/3

[56] References Cited

U.S. PATENT DOCUMENTS

| | | |
|---|---|---|
| 3,409,914 | 11/1968 | Jones . |
| 4,688,998 | 8/1987 | Olsen et al. . |
| 4,731,076 | 3/1988 | Noon et al. . |
| 4,779,614 | 10/1988 | Moise ........................................ 417/356 |
| 4,908,012 | 3/1990 | Moise et al. . |
| 4,957,504 | 9/1990 | Chardack . |
| 5,078,741 | 1/1992 | Bramm et al. . |
| 5,112,200 | 5/1992 | Isaacson et al. . |
| 5,147,388 | 9/1992 | Yamazaki . |
| 5,205,721 | 4/1993 | Isaacson ................................... 417/356 |
| 5,254,237 | 10/1993 | Snaper et al. . |
| 5,282,850 | 2/1994 | Davidson . |
| 5,290,227 | 3/1994 | Pasque . |
| 5,326,344 | 7/1994 | Bramm et al. ........................... 417/356 |
| 5,470,208 | 11/1995 | Kletschka . |
| 5,527,159 | 6/1996 | Bozeman, Jr. et al. . |
| 5,588,812 | 12/1996 | Taylor et al. . |
| 5,613,935 | 3/1997 | Jarvik . |

OTHER PUBLICATIONS

Stephen J. Mraz, "Giving The Heart A Helping Hand", Medical Industry Technology Focus, Feb. 8, 1996, Machine Design, pp. 35–39.

"Ventricle Assist Device (Vad or Heartpump)", Nasa–JSC Commercialization.

Nasa Patents Rotary Blood Pump (U.S. Patent No. 5,527, 159).

Gabriel Spera "Implantable Pumps Improve Drug Delivery, Strengthen Weak Hearts", R & D Horizons, Medical Device & Diagnostic Industry, Sep. 1997, pp. 55–64.

*Primary Examiner*—Ronald Capossela
*Attorney, Agent, or Firm*—Amster, Rothstein & Ebenstein

[57] ABSTRACT

An implantable electric pump for assisting blood flow in a patient in need thereof comprises a non-rotating pump housing and an electric motor enclosed within the housing, all motor components being disposed within the housing in a manner that does not substantially block blood flow through the central axial flow path. The motor comprises a stator and a rotor. The stator is fixedly mounted within the housing and contains a first set of electromagnetically interactive torque-generating components. The rotor is coaxially and rotatably disposed within the stator and has a rotor vane extending outwardly from a central longitudinal axis of the rotor towards the stator, and a second set of electromagnetically interacting torque-generating components disposed on the vane for rotation therewithin. The second set interacts with the first set to cause rotation of the rotor relative to the stator when a rotating electrical current is passed through the first set. The rotor vane has a configuration, height, and angled orientation which impart pumping force to blood within the central axial flow path when the rotor is rotated.

13 Claims, 4 Drawing Sheets

PEDIA-CADIO PUMP

FIELD OF THE INVENTION

This invention relates to the field of heart surgery, specifically open heart and heart replacement operations and, more particularly, to those in which infant or small animal are involved.

BACKGROUND OF THE INVENTION

Adult patients cart be instructed to remain quiescent while they are connected to intravenous, catheters, endotracheal tubes, and various monitoring devices. Infant victims of congenital heart disease and animal patients, on the other hand, cannot be expected to cooperate in such a situation, even if restrained, without continuous anesthesia or sedation. This anesthetized or sedated state cannot be continued indefinitely without producing a life-threatening situation of its own. Hence, it would be advantageous to be able to replace or supplement the heart's pumping action with an implant or multiple implants, at least until a suitable donor organ is obtained.

Many artificial hearts and heart booster devices ("ventricular assists") are known, but they nearly all depend upon some direct connection to the outside of the body through invasive surgical appliances. They are, however, primarily aimed at helping the patient to survive until a genetically compatible donor heart can be obtained. Research continues on implantable pumps or "ventricular assists," particularly for use whenever complete heart replacement is not indicated.

The evolution of such implantable devices has been paced by the state of the art technology. As microelectronic devices of extremely small size and reliability have been developed for communication, instrumentation, calculation and control, very complex miniature devices have been made possible. Rechargeable battery technology also has progressed considerably during recent years.

Accordingly, it is an object of the present invention to provide a fully implantable electric pump for assisting blood flow in a patient in need thereof.

Another object is to provide such a pump which is surgically insertable into, or parallel with, a ventricular outflow artery and causes at least some of the blood ejected by a ventricle to be forced through a central axial flow path of the pump.

A further object is to provide such a pump wherein the rotor is relatively freely rotatable by the blood flowing in the central axial flow path in the absence of any magnetic field within the stator—i.e., in case of an electrical failure in the pump.

Another object of the present invention is to provide such a pump which is relatively simple and inexpensive to manufacture, use and maintain.

SUMMARY OF THE INVENTION

It has now been discovered that the above and related objects of the present invention are obtained in an implantable electric pump for assisting blood flow in a patient need thereof. The pump comprises a non-rotating pump housing and an electric motor enclosed within the housing.

The non-rotating pump housing has an inner surface, two ends, and a central axial flow path passing therethrough, with an opening at each end of the housing for inflow and outflow of blood. All components of the electric motor enclosed within the housing are disposed within the housing in a manner that does not substantially block blood flow through the central axial flow path.

The motor comprises a stator and a rotor. The stator is fixedly mounted within the housing and contains a first set of electromagnetically interactive torque-generating components. The rotor is coaxially and rotatably disposed within the stator and has a rotor vane extending outwardly from a central longitudinal axis of the rotor towards the stator, and a second set of electromagnetically interacting torque-generating components disposed on the vane for rotation therewithin. The second set interacts with the first set to cause rotation of the rotor relative to the stator when a rotating electrical current is passed through the first set. The rotor vane has a configuration, height, and angled orientation which impart pumping force to blood within the central axial flow path when the rotor is rotated. The pump is surgically insertable into, or parallel with, a ventricular outflow artery to cause at least some of the blood ejected by a ventricle to flow through the central axial flow path.

In a preferred embodiment, the pump additionally includes first engaging means on the inner surface of the stator and second engaging means on the outer surface of the rotor, the first and second engaging means cooperatively limiting longitudinal and radial movement of the rotor relative to the stator. More particularly, the first engaging means may be a spaced apart pair of annular bushings, and the second engaging means may be a spaced apart pair of radial protrusions, one protrusion being disposed adjacent each end of the rotor and configured and dimensioned for receipt in a respective one of the annular bushings.

Preferably the rotor is relatively freely rotatable by the blood flowing in the central axial flow path in the absence of any magnetic field within the stator.

The present invention further encompasses an assembly comprising such a pump and means for creating a rotating magnetic field within the stator, thereby causing rotation of the rotor within the stator. The field-creating means may be external of the patient or include a rechargeable battery disposed within the housing.

BRIEF DESCRIPTION OF THE DRAWING

The above and related objects, features and advantages of the present invention will be more fully understood by reference to the following detailed description of the presently preferred, albeit illustrative, embodiments of the present invention when taken in conjunction with the accompanying drawing wherein.

DETAILED DESCRIPTION OF THE PREFERRED EMBODIMENTS

As an overview, the present invention comprises a miniaturized, implantable heart bridge/replacement pump that is small enough to be used in cases of very young infants or small animals. Even when power is lost, blood flow is not completely obstructed. Power for operation and control of the device is provided from outside the body by means of an electromagnetic field that is closely coupled to pickup coils incorporated in the implanted device. This power supply and control field serves to replenish the charge in a rechargeable battery through the pickup coils and a rectifier circuit that are part of the device, such that for short times the patient may be absent from the external power/control portion of the system. During such times the shaded-pole, brushless, alternating current motor that is built into the pump rotor and housing will continue to provide fluid pumping action with energy from the rechargeable battery by way of a switching electronics circuit that converts the direct current into an alternating current at a frequency that has been digitally set into the internal control electronics by a signal from the external control unit. This frequency control permits adjusting the pumping rate of the device without the necessity to resort to further surgically invasive procedures.

Figure 1:
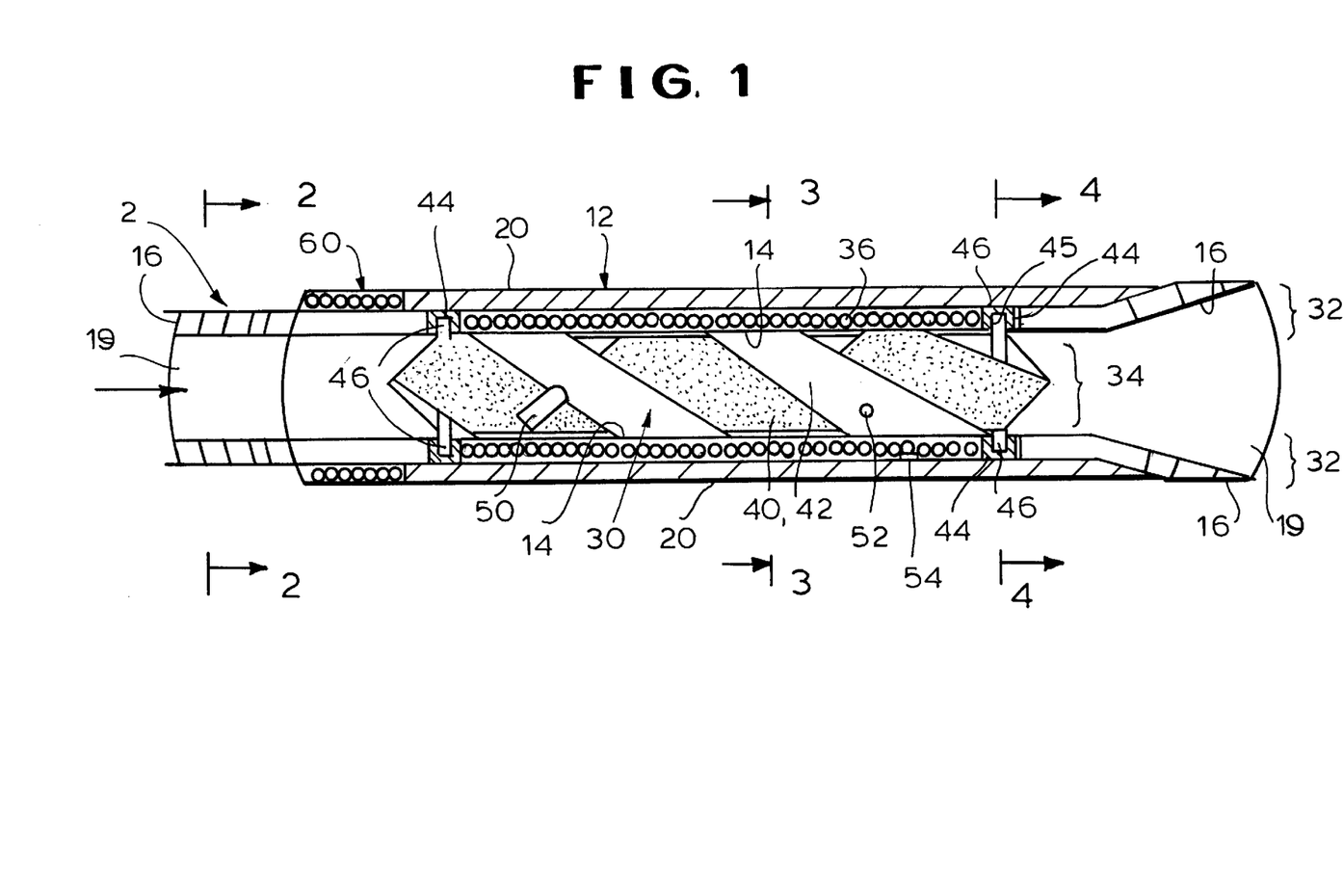
FIG. 1 is a cross sectional view of a pump according to the present invention.

Referring now to the drawing, and in particular to FIG. 1 thereof, therein illustrated in longitudinal cross-section is an implantable electric pump according to the present invention, generally designated by the reference numeral 10. The pump 10 comprises a non-rotating pump housing, generally designated 12, which housing defines an inner surface 14, two longitudinally opposed ends 16, and a central axial flow path 18 therethrough. An opening 19 is disposed at each end 16 of the housing in communication with the path 18 to enable the inflow and outflow of blood. Preferably, the housing 12 also includes a wrapped, flexible rechargeable battery 20 for reasons which will become apparent hereinafter.

In order to facilitate sewing of the housing 12 to the artery or vein in which it will be placed, the ends 16 of the housing 12 are preferably formed of GORTEX or a like water-impermeable, vapor-permeable, biocompatible material which can be sewn. Thus, the pump of the present invention avoids the "hose-clamp-like" methods of securing the pump to the artery or vein and enables the ends of device to actually be sutured to such artery or vein. This somewhat simplifies the surgical insertion procedure and, more importantly, reduces the probability of failure of the pump 10 by leakage and/or disconnection.

An electric motor, generally designated 30, is enclosed within the housing 12. The primary components of the electric motor are a stator, generally designated 32, and a rotor, generally designated 34.

The cylindrical stator 32 is fixedly mounted within the housing 10 and contains a first set of electromagnetically interactive torque-generating components 36. The inner surface of the stator 32 is biocompatible with blood and formed by stator windings which act as the first set of interactive torque-generating components 36. As will be explained hereinafter in further detail, a cylindrical electronics package 60 is preferably disposed at one end of the stator 32.

The rotor 34 is coaxially and rotatably disposed within the stator 32. The rotor 34 includes at least one rotor vane 40 extending outwardly from a central longitudinal axis of the rotor 34 towards the inner surface of the stator 32. Additionally, the rotor 34 contains a second set of electromagnetic interactive torque-generating components, preferably disposed on or as part of the rotor vane 40 for rotation therewith. Thus the rotor is preferably formed of a soft, magnetic material which is biocompatible with blood and acts as the second set of interactive torque-generating components.

Preferably, at least the outer surface of the rotor 34 and at least the inner surface of the stator 32 are made biocompatible, for example, by means of a plasma-arc deposited, anti-corrosive, relatively inert coating, such as titanium nitride, which is chemically inert to bodily fluids. Clearly, other anticorrosive, relatively inert coatings well known in the art may be deposited by conventional means to protect the pump from bodily fluids, and vice versa.

The second set of torque-generating components 42 interacts with the first set 36 of torque-generating components to cause flotation and rotation of the rotor 34 relative to the stator 32 when electric current is passed through the first set 36 to create a rotating magnetic field.

The pump central axial flow path 18 is bounded radially by the central longitudinal axis of the rotor 34 (which is the same for the stator 32 and housing 12) and the inner surface of the stator 32, and the rotor vane 40 has a configuration, height and angled orientation which imparts a pumping force to the blood within the central axial flow path when the rotor vane 40 is rotated. The pump is surgically insertable into, or parallel with, a ventricular outflow artery to cause at least some of the blood ejected by a ventricle to flow through the central axial flow path.

It will be appreciated by those skilled in the art that the rotor 34 may be composed of not just a single helical rotor vane 40, as illustrated, but by a plurality of helical rotor vanes, each preferably extending the full length of the rotor 34. While the rotor vane 40 may be of constant height throughout its length, as illustrated, it preferably tapers somewhat inwardly in the downstream direction.

The inner surface of the rotor vane 40—that is, the surface of the rotor vane 40 closest to the central longitudinal axis of the rotor 34 (and hence the stator 34 and the housing 12)—extends relatively closely to the central longitudinal axis. At the same time, it will be appreciated by those skilled in the art that the rotating vane 40 will affect the blood disposed inwardly thereof (that is, along the central longitudinal axis) and cause axial flow thereof. The outer surface of the helical rotor vane 40—that is, the surface of the rotor vane farthest from the central longitudinal axis—is closest to the inner surface of the stator 32.

In the preferred embodiment illustrated, the stator 32 includes adjacent each end of the rotor 34 an annular bushing 44 defining a circumferential recess 45 on its inner surface, and the rotor 34 includes a radially outwardly extending (preferably circumferential) projection 46 on its outer surface adjacent each end thereof. Each projection 46 is configured and dimensioned to be at least partially received within the recess 45 of a respective annular bushing 44. The bushings 44 and the projections 46 form first and second engaging means, respectively, with the first and second engaging means cooperatively limiting relative longitudinal and radial movement of the rotor 34 relative to the stator 32. More particularly, the first engaging means is a spaced apart pair of the annular bushings 44 on the stator 32, and the second engaging means is a spaced apart pair of the radial protrusions 46 on the rotor 34. Typically, the inner diameter of the stator 32 (except for recesses 45) only slightly exceeds the outer diameter of the rotor 34 (except for protrusions 46).

It will be appreciated that the cooperation of the first and second engaging means 44 and 45 performs two separate and distinct functions. First, it prevents relative longitudinal movement of the rotor 34 and the stator 32. Second, it assists in maintaining the rotor 34 in its coaxial position within the stator 32, closely spaced from the inner surface of the stator 32. Both functions are performed through physical means and thus regardless of whether or not the magnetic field of the stator 32 is energized or de-energized. Accordingly, the rotor 34 i,; relatively freely rotatable by the blood flowing in the central axial flow path 18 in the absence of any magnetic field within the stator 32, the blood having only to overcome the frictional resistance, if any, of the rotor protrusions 46 within the stator recesses 45 (of annular bearings 44). Thus an electrical failure of the power supply for the stator 32 does not result in a blockage or significant impediment to flow of the blood through the pump 10. The inertia and friction of the rotor 34 with the stator 32, and the inclination angle (pitch) of the rotor vane 40, are selected such that normal blood flow in an artery would cause the rotor 34 to rotate, even in the absence of any rotating electric field in the stator 32, such that the blood flow through the pump 10 would exhibit some pressure drop, but not enough of a drop to cause circulatory collapse.

If desired for particular applications, the width and/or depth of the recess 45 of each annular bearing 44 may slightly exceed the width and/or height of each projection 46 so as to enable controlled maximum relative longitudinal and/or radial motion.

A single, offset, shorted turn of highly conductive material 50, such as silver or copper, is built into the rotor 34 to form a "shaded pole" rotor. This permits a brushless motor action with a predicable starting direction, thus providing a reliable flow direction 18. This flow direction can be permanently engraved as a prominent marker on the outside of the stator in order to reduce the probability of implanting the device in the wrong directions in an artery or vein.

With a slight amount of "slip", the rotor 34 turns at a little less than the "synchronous speed" of an alternating current motor. A tiny chunk of rare earth or like permanent-magnet material 52 is embedded at an appropriate location in the rotor 34 and induces a brief pulse of current in a detector circuit 54. The detector circuit 54 may simply be a multiple turn pickup coil of fine wire placed in the stator 32 such that the magnetic field of the tiny magnet in the rotor 34 cuts the turns of pickup coil 54 once for each revolution of the rotor 34. This rotation signal can be telemetered externally of the patient by a data link built into an electronics package within the stator 32 and permits initiating an alarm in the event that the pumping action slows down or ceases. The rotation signal also can confirm the actual rotor speed, and hence the demanded flow rate, to external frequency control circuits that set the frequency of the alternating current that supplies the stator field through the stator windings 36 positioned around the rotor 34.

The device provides controlled, fluid pumping action with energy from the wrapped, flexible, rechargeable battery 20 of the stator 32 by way of the switching electronics (housed in cylindrical electronics package 60 on the stator 32) that converts he direct current of the battery 20 into an alternating current at a frequency that has been digitally set and telemetered into the internal control electronics package 60 by a signal from an external unit. This frequency control permits adjusting the pumping rate of the device without the necessity for resorting to further surgically invasive procedures.

Figure 2:
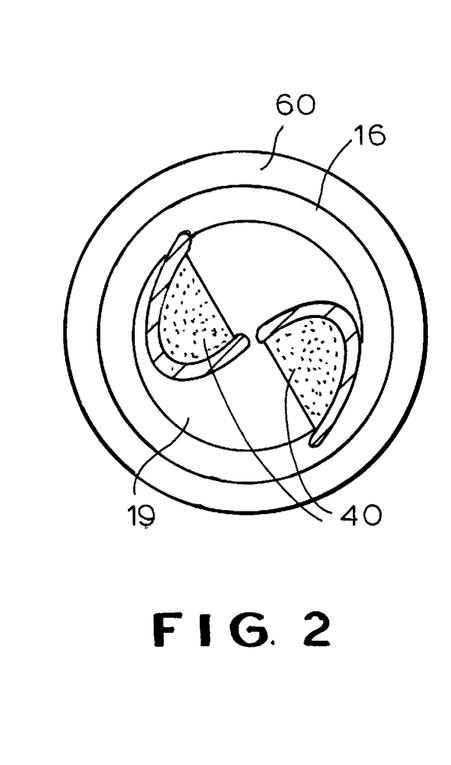
FIG. 2 is a transverse sectional view thereof taken along the line 2—2 of FIG. 1.

Referring now to FIG. 2, therein illustrated is a block diagram of the electronic system within the implanted pump 10. High frequency electromagnetic energy 130 from outside the patient is picked up by the small pickup coils 131, which form a parallel resonant circuit with a tuning adjustment variable capacitor 132. The received voltage is rectified via a bridge rectifier circuit 133, which supplies direct charging current to the rechargeable storage battery 20.

The positive, minus and central terminals of the battery 20 supply all the energy for operation of the device 10. The direct current is fed through the motor control electronics 135 to the internal adjustable frequency motor drive oscillator 136. The frequency of the internal motor drive oscillator 136 (and its starting and stopping signals for pulsed pumping operation) are controlled by signals 137 sent from the internal motor control electronics 135 to the internal motor drive oscillator 136. The output of the internal motor drive oscillator 136 is fed through the field coils 36 of stator 32 to produce a schematically indicated rotating magnetic field 142, that cause the rotor 34 to spin.

The telemetering magnet 52 and pickup coil 54 provide a pulse to a telemetry encoder/transmitter 140 in the stator 32. The pulse signals are encoded, preferably redundantly in order to reliably pierce through the various electromagnetic "noises" commonly found in intensive care and surgical units. These feedback signals are sent, via a telemetry coil 141, to a telemetry pickup coil 126 external to the patient (see FIG. 3). An external control and monitoring unit 122 (see FIG. 3) can send a coded signal via the telemetry link that will set the motor field coil frequency to a desired value and will set the counters in its own circuits to monitor the pulse count for the rate that corresponds to the desired rotational rate. By sending start and stop signals to the internal motor control electronics 135, the external control unit 122 can cause a "beating" action or pulse of blood flow to simulate that of the normal heart. In the case of a multiplicity of "ventricular assist" units being implanted in the various arteries around the heart, the external control unit 122 can so synchronize them that they simulate the beating of a normal heart, as required for older infants—that is, it can control the pumps to operate, alternately, in bursts of pumping action in a rhythm to simulate the actions of the left and right ventricles of the heart.

Figure 3:
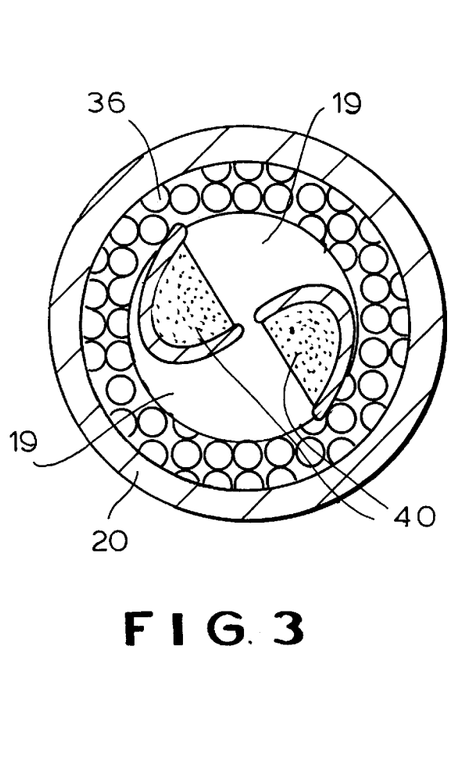
FIG. 3 is a transverse sectional view thereof taken along the line 3—3 of FIG. 1.
Figure 4:
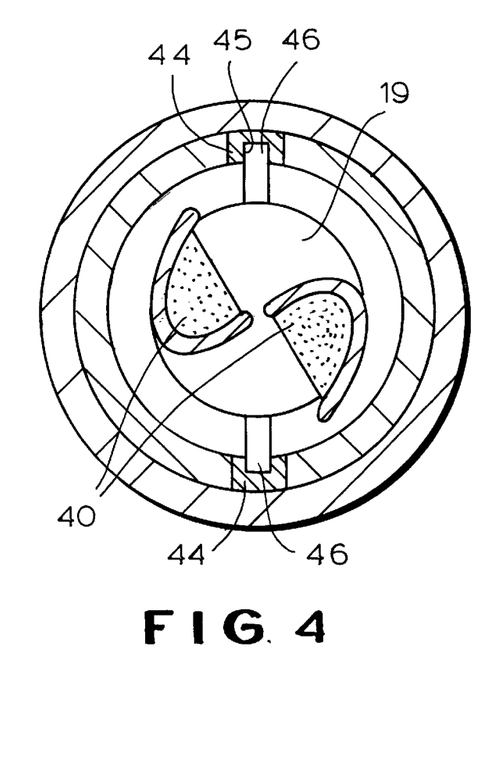
FIG. 4 is a transverse sectional view thereof taken along the line 4—4 of FIG. 1.
Figure 5:
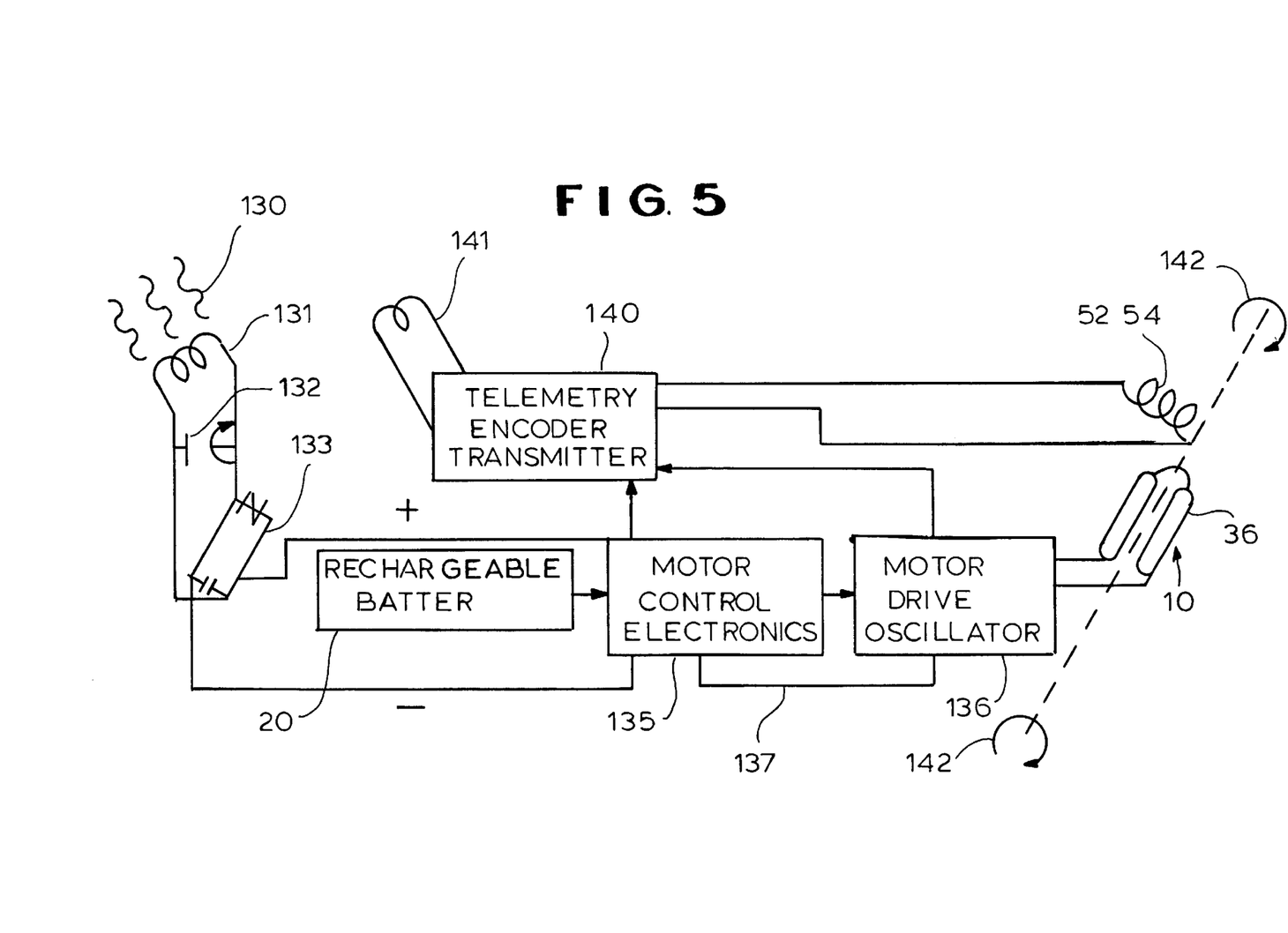
FIG. 5 is a block diagram of the internal electronic system contained within the implanted pump.
Figure 6:
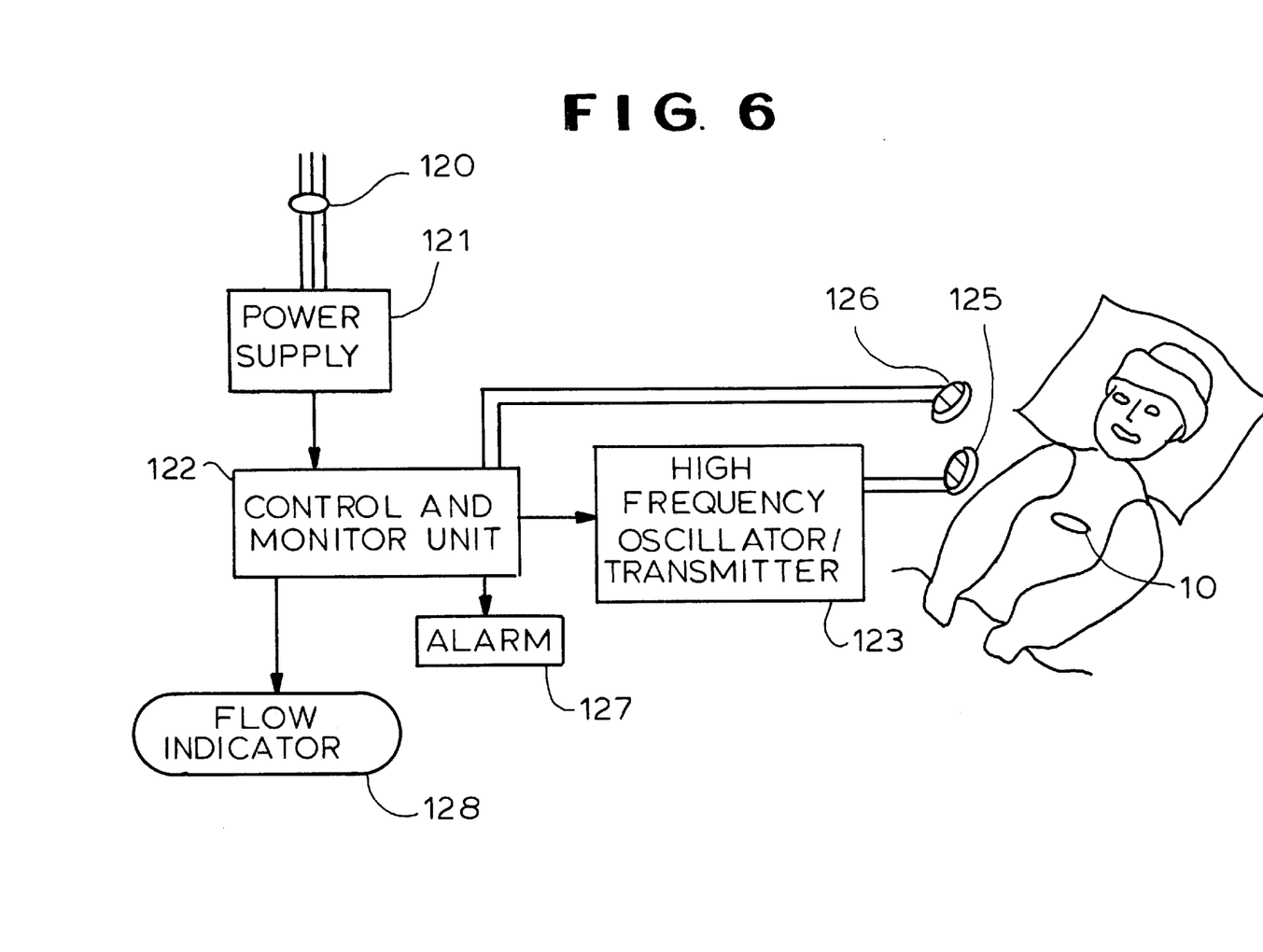
FIG. 6 is a block diagram of the external power and control system for the implanted pump.

Referring now to FIG. 3, therein illustrated is a block diagram of the electronic system outside the patient. Electrical power taken from a three pronged wall plug 120 is fed via a conventional transformer/rectifier/filter power supply unit 121 to control and monitor circuits within the external control and monitor unit 122. The external control unit 122 provides power and a frequency control signal to an external high frequency power oscillator/transmitter 123. This high frequency energy is coupled into the patient unit (i.e., the implanted pump 10) via a body coil 125.

The rotation pulse signal from the internal telemetry encoder/transmitter 140 and telemetry coil 141 (see FIG. 2) is received by the external telemeter pickup coil 126, whence it goes to the circuits of the external control and monitor unit 122. If rotation, as observed, slows below a set rate previously entered in a counter in the external control unit 122, an alarm 127 is activated to summon the help of intensive care attendants. Normally, the rotation rate is counted and compared to the set count per second. The flow rate, represented by the rotation signal, is preferably displayed on a flow indicator 128.

Energy to operate all of the subsystems within the implanted device 10 is supplied to the internal rechargeable battery 20 through an external high-frequency power oscillator-transmitter 123 that drives a body coil 125 which can be placed around the patient to couple into a secondary coil in the electronics package 60 of the stator 32. The frequency of the power oscillator-transmitter 123 is such that the receiving coil 131 (see FIG. 2) within the electronics package 60 is resonant to it, and such that the other coils in the assembly present high inductive reactance to the high frequency electromagnetic field of the body coil 125.

The device can be made in a selection of physical sizes so that it might be adapted for use in adults and even large animals as well as infants and small animals.

To summarize, the present invention provides a fully implantable electric pump for assisting blood flow in a patient in need thereof, the pump being surgically insertable into (or in parallel with) a ventricular outflow artery and causing at least some of the blood ejected by a ventricle to be forced through a central axial path of the pump. The rotor of the pump is relatively freely rotatable by the blood flowing in the central axial flow path in the absence of any magnetic field within the stator (that is, in case of an electric failure of the pump). The pump is relatively simple and inexpensive to manufacture, use and maintain.

Now that the preferred embodiments of the present invention have been shown and described in detail, various modifications and improvements thereon will become readily apparent to those skilled in the art. Accordingly, the spirit and scope of the present invention is to be construed broadly and limited only by the appended claims, and not by the foregoing specification.

I claim:

1. An implantable electric pump for assisting blood flow in a patient in need thereof, said pump comprising:
    (1) a non-rotating pump housing having an inner surface, two ends, and a central axial flow path passing therethrough, with an opening at each said end of said housing for inflow and outflow of blood; and
    (2) an electric motor enclosed within said housing, all components of said motor being disposed within said housing in a manner that does not substantially block blood flow through the central axial flow path, wherein said motor comprises:
        (a) a stator fixedly mounted within said housing and containing a first set of electromagnetically interactive torque-generating components;
        (b) a rotor coaxially and rotatably disposed within said stator, said rotor having:
            (i) a rotor vane extending outwardly towards said stator, and
            (ii) a second set of electromagnetically interacting torque-generating components disposed on said vane for rotation therewith, said second set interacting with said first set to cause rotation of said rotor relative to said stator when electrical current is passed through said first set;
        the pump central axial flow path being bounded by a central longitudinal axis of said rotor and said inner surface of said stator, and said rotor vane having a configuration, height, and angled orientation which impart pumping force to blood within the central axial flow path when said rotor is rotated;
        said pump being surgically insertable into, or parallel with, a ventricular outflow artery to cause at least some of the blood ejected by a ventricle to flow through the central axial flow path; and
        (c) first engaging means adjacent an inner surface of said stator and second engaging means adjacent an outer surface of said rotor, said first and second engaging means cooperatively limiting longitudinal and radial movement of said rotor relative to said stator.

2. The pump of claim 1 wherein said first engaging means is a spaced apart pair of annular bushings and said second engaging means is a spaced apart pair of radial protrusions, one protrusion disposed adjacent each end of said rotor and each protrusion being configured and dimensioned for receipt in a respective one of said annular bushings.

3. The pump of claim 1 wherein said rotor is relatively freely rotatable by the blood flowing in the central axial flow path in the absence of any magnetic field within said stator.

4. The pump of claim 1 wherein said rotor vane extends helically about a longitudinal axis of said rotor.

5. The pump of claim 1 wherein said rotor essentially consists of said rotor vane and said second set.

6. An assembly comprising the pump of claim 1 and means for creating a rotating magnetic field within said stator, thereby causing rotation of said rotor within said stator.

7. The assembly of claim 6 wherein said field-creating means is external of the patient.

8. The assembly of claim 6 wherein said field-creating means includes a rechargeable battery disposed within said housing.

9. The pump of claim 1 wherein said rotor is hollow and consists essentially of said vane and said second set.

10. An implantable electric pump for assisting blood flow in a patient in need thereof, said pump comprising:
    (1) a non-rotating pump housing having an inner surface, two ends, and a central axial flow path passing therethrough, with an opening at each said end of said housing for inflow and outflow of blood; and
    (2) an electric motor enclosed within said housing, all components of said motor being disposed within said housing in a manner that does not substantially block blood flow through the central axial flow path, wherein said motor comprises:
        (a) a stator fixedly mounted within said housing and containing a first set of electromagnetically interactive torque-generating components;
        (b) a rotor coaxially and rotatably disposed within said stator, said rotor having:
            (i) a rotor vane extending outwardly towards said stator, and
            (ii) a second set of electromagnetically interacting torque-generating components disposed on said vane for rotation therewith, said second set interacting with said first set to cause rotation of said rotor relative to said stator when electrical current is passed through said first set, and
            (iii) first engaging means adjacent an inner surface of said stator and second engaging means adjacent an outer surface of said rotor; said first and second engaging means cooperatively limiting longitudinal and radial movement of said rotor relative to said stator;
        the pump central axial flow path being bounded by a central longitudinal axis of said rotor and said inner surface of said stator, and said rotor vane having a configuration, height, and angled orientation which impart pumping force to blood within the central axial flow path when said rotor is rotated;
        said rotor vane extending helically about a longitudinal axis of said rotor and said rotor being devoid of any outer cylindrical wall about said rotor vane and relatively freely rotatable by the blood flowing in the central axial flow path in the absence of any magnetic field within said stator; and said pump being surgically insertable into, or parallel with, a ventricular outflow artery to cause at least some of the blood ejected by a ventricle to flow through the central axial flow path.

11. The pump of claim 10 wherein said first engaging means is a spaced apart pair of annular bushings and said second engaging means is a spaced apart pair of radial protrusions, one protrusion disposed adjacent each end of said rotor and each protrusion being configured and dimensioned for receipt in a respective one of said annular bushings.

12. An assembly comprising the pump of claim 10 and means for creating a rotating magnetic field within said stator, thereby causing rotation of said rotor within said stator.

13. An implantable electric pump for assisting blood flow in a patient in need thereof, said pump comprising:
 (1) a non-rotating pump housing having an inner surface, two ends, and a central axial flow path passing therethrough, with an opening at each said end of said housing for inflow and outflow of blood; and
 (2) an electric motor enclosed within said housing, all components of said motor being disposed within said housing in a manner that does not substantially block blood flow through the central axial flow path, wherein said motor comprises:
  (a) a stator fixedly mounted within said housing and containing a first set of electromagnetically interactive torque-generating components;
  (b) a hollow rotor coaxially and rotatably disposed within said stator, said rotor consisting essentially of:
   (i) a rotor vane extending outwardly towards said stator, and
   (ii) a second set of electromagnetically interacting torque-generating components disposed on said vane for rotation therewith, said second set interacting with said first set to cause rotation of said rotor relative to said stator when electrical current is passed through said first set;
  the pump central axial flow path being bounded by a central longitudinal axis of said rotor and said inner surface of said stator, and said rotor vane having a configuration, height, and angled orientation which impart pumping force to blood within the central axial flow path when said rotor is rotated;
  said pump being surgically insertable into, or parallel with, a ventricular outflow artery to cause at least some of the blood ejected by a ventricle to flow through the central axial flow path.

* * * * *

UNITED STATES PATENT AND TRADEMARK OFFICE
CERTIFICATE OF CORRECTION

PATENT NO. : 6,042,347
DATED : March 28, 2000
INVENTOR(S) : Scholl et al.

It is certified that error appears in the above-indentified patent and that said Letters Patent is hereby corrected as shown below:

Item [54],

ON THE TITLE PAGE, delete "PEDIA-CADIO" and add -- PEDIA-CARDIO--.

Signed and Sealed this

Sixth Day of February, 2001

Attest:

Q. TODD DICKINSON

*Attesting Officer*   *Director of Patents and Trademarks*